(12) United States Patent
Nieto et al.

(10) Patent No.: US 10,864,661 B2
(45) Date of Patent: *Dec. 15, 2020

(54) DEVICE AND METHOD FOR MAKING A VARIABLE SURFACE BREAST IMPLANT

(71) Applicant: Allergan, Inc., Irvine, CA (US)

(72) Inventors: Robert L. Nieto, Santa Barbara, CA (US); Claudia Renteria, Goleta, CA (US); Phat Ngo, Goleta, CA (US); David Schuessler, Santa Ana, CA (US); Dennis Van Epps, Goleta, CA (US)

(73) Assignee: ALLERGAN, INC., Irvine, CA (US)

( * ) Notice: Subject to any disclaimer, the term of this patent is extended or adjusted under 35 U.S.C. 154(b) by 489 days.

This patent is subject to a terminal disclaimer.

(21) Appl. No.: 15/629,635

(22) Filed: Jun. 21, 2017

(65) Prior Publication Data

US 2017/0290652 A1 Oct. 12, 2017

Related U.S. Application Data

(63) Continuation of application No. 14/106,524, filed on Dec. 13, 2013, now Pat. No. 9,688,006.

(Continued)

(51) Int. Cl.
*B29C 41/40* (2006.01)
*B29C 41/14* (2006.01)
(Continued)

(52) U.S. Cl.
CPC ............ *B29C 41/40* (2013.01); *A61F 2/0077* (2013.01); *A61F 2/12* (2013.01); *B05D 1/18* (2013.01); *B05D 5/02* (2013.01); *B29C 37/0053* (2013.01); *B29C 41/02* (2013.01);

*B29C 41/025* (2013.01); *B29C 41/14* (2013.01); *B29C 41/34* (2013.01); *B29C 41/38* (2013.01);
(Continued)

(58) Field of Classification Search
CPC ....... B29C 41/025; B29C 41/08; B29C 41/14; B29C 41/34; B29C 41/38; B29C 41/40; B29C 45/2614; B29C 41/085; B29C 41/10; B29C 41/20
USPC ......................... 264/301, 305, 306
See application file for complete search history.

(56) References Cited

U.S. PATENT DOCUMENTS

| 2,324,735 A | 7/1943 | Spanel |
| 2,762,476 A | 9/1956 | Barnett |

(Continued)

FOREIGN PATENT DOCUMENTS

| CA | 2049377 | 3/1992 |
| CA | 2811975 | 11/2011 |

(Continued)

OTHER PUBLICATIONS

Alvarez, Sonia et al, Synthesis of Macro/Mesoporous Silica and Carbon Monoliths by Using a Commercial Polyurethane Foam as Sacrificial Template, Material Letters, 2007, 2378-2381, 61.

(Continued)

*Primary Examiner* — Atul P. Khare
(74) *Attorney, Agent, or Firm* — Nathan S. Smith; Sujohn Das; Morgan, Lewis & Bockius LLP

(57) ABSTRACT

Devices and methods are provided for making a variable textured breast implant when used in conjunction with a breast implant mandrel having a molding surface and a stem depending therefrom.

15 Claims, 9 Drawing Sheets

Related U.S. Application Data

(60) Provisional application No. 61/736,687, filed on Dec. 13, 2012.

(51) Int. Cl.

| | | |
|---|---|---|
| *A61F 2/12* | (2006.01) | |
| *B29C 41/02* | (2006.01) | |
| *B29C 37/00* | (2006.01) | |
| *B29C 41/34* | (2006.01) | |
| *B05D 1/18* | (2006.01) | |
| *B05D 5/02* | (2006.01) | |
| *B29C 41/38* | (2006.01) | |
| *A61F 2/00* | (2006.01) | |
| *B29C 41/08* | (2006.01) | |
| *B29L 31/00* | (2006.01) | |

(52) U.S. Cl.
CPC ......... *A61F 2240/001* (2013.01); *B29C 41/08* (2013.01); *B29C 2791/001* (2013.01); *B29K 2995/0072* (2013.01); *B29L 2031/7532* (2013.01)

(56) References Cited

U.S. PATENT DOCUMENTS

| | | |
|---|---|---|
| 2,805,208 A | 9/1957 | Roche |
| 3,189,921 A | 6/1965 | Pangman |
| 3,293,663 A | 12/1966 | Cronin |
| 3,366,975 A | 2/1968 | Pangman |
| 3,559,214 A | 2/1971 | Pangman |
| 3,600,718 A | 8/1971 | Boone |
| 3,665,520 A | 5/1972 | Perras et al. |
| 3,700,380 A | 10/1972 | Kitrilakis |
| 3,852,832 A | 12/1974 | McGhan et al. |
| 3,934,274 A | 1/1976 | Hartley |
| 3,967,051 A * | 6/1976 | Moore ................ H01B 17/28 174/143 |
| 4,034,751 A | 7/1977 | Hung |
| 4,102,360 A * | 7/1978 | Hopkins ............. F16L 11/045 138/125 |
| 4,157,085 A | 6/1979 | Austad |
| 4,231,979 A | 11/1980 | White et al. |
| 4,237,237 A | 12/1980 | Jarre et al. |
| 4,264,990 A | 5/1981 | Hamas |
| 4,298,997 A | 11/1981 | Rybka |
| 4,298,998 A | 11/1981 | Naficy |
| 4,329,385 A | 5/1982 | Banks |
| 4,428,082 A | 1/1984 | Naficy |
| 4,433,440 A | 2/1984 | Cohen |
| 4,470,160 A | 9/1984 | Cavon |
| 4,482,577 A | 11/1984 | Goldstein et al. |
| 4,499,211 A | 2/1985 | Walch et al. |
| 4,531,244 A | 7/1985 | Hamas |
| 4,533,568 A | 8/1985 | McClinton et al. |
| 4,573,999 A | 3/1986 | Netto |
| 4,584,324 A | 4/1986 | Bauman et al. |
| 4,592,755 A | 6/1986 | Penton et al. |
| 4,608,396 A | 8/1986 | Bauman et al. |
| 4,610,690 A | 9/1986 | Tiffany |
| 4,636,213 A | 1/1987 | Pakiam |
| 4,643,733 A | 2/1987 | Becker |
| 4,647,618 A | 3/1987 | Bauman et al. |
| 4,648,880 A | 3/1987 | Brauman |
| 4,650,487 A | 3/1987 | Chaglassian |
| 4,651,717 A | 3/1987 | Jakubczak |
| 4,681,587 A | 7/1987 | Eberl et al. |
| 4,740,208 A | 4/1988 | Cavon |
| 4,772,285 A | 9/1988 | Ksander et al. |
| 4,773,908 A | 9/1988 | Becker |
| 4,773,909 A | 9/1988 | Chaglassian |
| 4,790,848 A | 12/1988 | Cronin |
| 4,795,464 A | 1/1989 | Eberl et al. |
| 4,803,025 A | 2/1989 | Brockmeyer |
| 4,828,560 A | 5/1989 | Heyler |
| 4,840,628 A | 6/1989 | Cavon |
| 4,841,992 A | 6/1989 | Sasaki et al. |
| 4,859,383 A | 8/1989 | Dillon |
| 4,859,712 A | 8/1989 | Cox |
| 4,889,744 A | 12/1989 | Quaid |
| 4,899,764 A | 2/1990 | Gauger |
| 4,902,294 A | 2/1990 | Gosserez |
| 4,906,423 A | 3/1990 | Frisch |
| 4,936,858 A | 6/1990 | O'Keeffe |
| 4,944,749 A | 7/1990 | Becker |
| 4,944,750 A | 7/1990 | Cox |
| 4,950,292 A | 8/1990 | Audretsch |
| 4,955,907 A | 9/1990 | Ledergerber |
| 4,955,909 A | 9/1990 | Ersek et al. |
| 4,960,425 A | 10/1990 | Yan et al. |
| 4,963,150 A | 10/1990 | Brauman |
| 4,965,430 A | 10/1990 | Curtis et al. |
| 4,969,899 A | 11/1990 | Cox |
| 5,002,572 A | 3/1991 | Picha |
| 5,007,929 A | 4/1991 | Quaid |
| 5,007,940 A | 4/1991 | Berg |
| 5,011,494 A | 4/1991 | von Recum et al. |
| 5,022,942 A | 6/1991 | Yan et al. |
| 5,026,394 A | 6/1991 | Baker |
| 5,034,422 A | 7/1991 | Triolo et al. |
| 5,035,249 A | 7/1991 | Sasaki et al. |
| 5,092,348 A | 3/1992 | Dubrul et al. |
| 5,092,882 A | 3/1992 | Lynn et al. |
| 5,104,409 A | 4/1992 | Baker |
| 5,116,370 A | 5/1992 | Foglietti |
| 5,116,387 A | 5/1992 | Berg |
| 5,128,088 A | 7/1992 | Shimomura et al. |
| 5,135,959 A | 8/1992 | Hill |
| 5,146,933 A | 9/1992 | Boyd |
| 5,147,398 A | 9/1992 | Lynn |
| 5,158,571 A | 10/1992 | Picha |
| 5,158,573 A | 10/1992 | Berg |
| 5,171,269 A | 12/1992 | Bark |
| 5,185,297 A | 2/1993 | Park |
| 5,204,024 A | 4/1993 | Onaka et al. |
| 5,207,709 A | 5/1993 | Picha |
| 5,219,361 A | 6/1993 | von Recum et al. |
| 5,236,453 A | 8/1993 | Picha |
| 5,236,454 A | 8/1993 | Miller |
| 5,236,457 A | 8/1993 | Devanathan |
| 5,246,454 A | 9/1993 | Peterson |
| 5,282,856 A | 2/1994 | Ledergerber |
| 5,296,069 A | 3/1994 | Robert |
| 5,320,364 A * | 6/1994 | Mistrater ............ B23B 31/1175 198/803.7 |
| 5,340,656 A | 8/1994 | Sachs et al. |
| 5,348,788 A | 9/1994 | White |
| 5,354,338 A | 10/1994 | Ledergerber |
| 5,356,429 A | 10/1994 | Seare |
| 5,358,521 A | 10/1994 | Shane |
| 5,376,117 A | 12/1994 | Pinchuk |
| 5,383,929 A | 1/1995 | Ledergerber |
| 5,437,824 A | 8/1995 | Carlisle |
| 5,441,919 A | 8/1995 | Park |
| 5,447,535 A | 9/1995 | Muller |
| 5,455,100 A | 10/1995 | White |
| 5,480,430 A | 1/1996 | Carlisle et al. |
| 5,496,367 A | 3/1996 | Fisher |
| 5,496,370 A | 3/1996 | Hamas |
| 5,507,808 A | 4/1996 | Becker |
| 5,522,896 A | 6/1996 | Prescott |
| 5,525,275 A | 6/1996 | Iversen et al. |
| 5,534,023 A | 7/1996 | Henley |
| 5,545,217 A | 8/1996 | Offray |
| 5,545,220 A | 8/1996 | Andrews et al. |
| 5,549,671 A | 8/1996 | Waybright et al. |
| 5,571,179 A | 11/1996 | Manders |
| RE35,391 E | 12/1996 | Brauman |
| 5,589,176 A | 12/1996 | Seare, Jr. |
| 5,605,693 A | 2/1997 | Seare |
| 5,607,473 A | 3/1997 | Weber-Unger |
| 5,624,674 A | 4/1997 | Seare |
| 5,630,843 A | 5/1997 | Rosenberg |
| 5,630,844 A | 5/1997 | Dogan |

(56) References Cited

U.S. PATENT DOCUMENTS

| | | | |
|---|---|---|---|
| 5,653,755 A | 8/1997 | Ledergerber |
| 5,658,330 A | 8/1997 | Carlisle |
| 5,674,285 A | 10/1997 | Quaid |
| 5,681,572 A | 10/1997 | Seare |
| 5,776,159 A | 7/1998 | Young |
| 5,779,734 A | 7/1998 | Ledergerber |
| 5,798,065 A | 8/1998 | Picha |
| 5,824,081 A | 10/1998 | Knapp |
| 5,843,189 A | 12/1998 | Perouse |
| 5,855,588 A | 1/1999 | Young |
| 5,871,497 A | 2/1999 | Young |
| 5,895,423 A | 4/1999 | Becker et al. |
| 5,935,164 A | 8/1999 | Iverson |
| 5,961,552 A | 10/1999 | Iversen et al. |
| 5,964,803 A | 10/1999 | Iversen et al. |
| 5,965,076 A | 10/1999 | Banks |
| 5,984,943 A | 11/1999 | Young |
| 5,993,716 A | 11/1999 | Draenert |
| 6,071,309 A | 6/2000 | Knowlton |
| 6,074,421 A | 6/2000 | Murphy |
| 6,083,262 A | 7/2000 | Caravel |
| 6,099,565 A | 8/2000 | Sakura |
| 6,113,634 A | 9/2000 | Weber-Unger |
| 6,146,418 A | 11/2000 | Berman |
| 6,183,514 B1 | 2/2001 | Becker |
| 6,187,043 B1 | 2/2001 | Ledergerber |
| 6,203,570 B1 | 3/2001 | Baeke |
| 6,206,930 B1 | 3/2001 | Burg |
| 6,214,045 B1 | 4/2001 | Corbitt, Jr. et al. |
| 6,214,926 B1 | 4/2001 | Winn |
| 6,232,374 B1 | 5/2001 | Liu et al. |
| 6,315,796 B1 | 11/2001 | Eaton |
| 6,340,648 B1 | 1/2002 | Imura et al. |
| 6,387,133 B1 | 5/2002 | Perouse |
| 6,432,138 B1 | 8/2002 | Offray |
| 6,464,726 B1 | 10/2002 | Heljenek |
| 6,507,990 B1* | 1/2003 | Moreno ............... H02K 15/024  29/525 |
| 6,520,989 B1 | 2/2003 | Eaton |
| 6,531,523 B1 | 3/2003 | Davankov |
| 6,544,287 B1 | 4/2003 | Johnson et al. |
| 6,602,452 B2 | 8/2003 | Schuessler |
| 6,605,116 B2 | 8/2003 | Falcon |
| 6,638,308 B2 | 10/2003 | Corbitt et al. |
| 6,673,285 B2 | 1/2004 | Ma |
| 6,692,527 B1 | 2/2004 | Bellin et al. |
| 6,743,254 B2 | 6/2004 | Guest et al. |
| 6,755,861 B2 | 6/2004 | Nakao |
| 6,802,861 B1 | 10/2004 | Hamas |
| 6,811,570 B1 | 11/2004 | Gehl |
| 6,818,673 B2 | 11/2004 | Ferguson |
| 6,875,233 B1 | 4/2005 | Turner |
| 6,881,226 B2 | 4/2005 | Corbitt |
| 6,900,055 B1 | 5/2005 | Fuller et al. |
| 6,913,626 B2 | 7/2005 | McGhan |
| 6,916,339 B1 | 7/2005 | Missana |
| 6,921,418 B2 | 7/2005 | Ledergerber |
| 6,932,840 B1 | 8/2005 | Bretz |
| 6,993,406 B1 | 1/2006 | Cesarano, III |
| 7,081,135 B2 | 7/2006 | Smith |
| 7,081,136 B1 | 7/2006 | Becker |
| 7,105,116 B2 | 9/2006 | Bellin et al. |
| 7,169,180 B2 | 1/2007 | Brennan |
| 7,192,450 B2 | 3/2007 | Brauker |
| 7,244,270 B2 | 7/2007 | Lesh |
| 7,268,169 B2 | 9/2007 | Hirayma et al. |
| 7,309,232 B2 | 12/2007 | Rutherford et al. |
| 7,323,208 B2 | 1/2008 | Ma |
| 7,476,249 B2 | 1/2009 | Frank |
| 7,520,896 B2 | 4/2009 | Benslimane |
| 7,547,393 B2 | 6/2009 | Ramaswamy |
| 7,625,405 B2 | 12/2009 | Purkait |
| 7,632,228 B2 | 12/2009 | Brauker |
| 7,632,291 B2 | 12/2009 | Stephens et al. |
| 7,641,688 B2 | 1/2010 | Lesh |
| 7,645,475 B2 | 1/2010 | Prewett |
| 7,758,788 B2 | 7/2010 | Job |
| 7,867,061 B2 | 1/2011 | Elshout |
| 8,202,317 B2 | 6/2012 | Becker |
| 8,313,527 B2 | 11/2012 | Powell et al. |
| 8,409,279 B2 | 4/2013 | Freund |
| 8,487,012 B2 | 7/2013 | Goraltchouk et al. |
| 8,506,627 B2 | 8/2013 | Van Epps et al. |
| 8,546,458 B2 | 10/2013 | Thompson et al. |
| 8,556,968 B2 | 10/2013 | Hamas et al. |
| 8,562,677 B2 | 10/2013 | Job |
| 8,597,012 B2* | 12/2013 | Shah ............... B05C 11/00  264/215 |
| 8,679,279 B2 | 3/2014 | Thompson et al. |
| 8,685,296 B2 | 4/2014 | Liu et al. |
| 8,728,159 B2 | 5/2014 | Kim |
| 8,765,039 B1 | 7/2014 | Ledergerber |
| 8,801,782 B2 | 8/2014 | Nofrey et al. |
| 8,808,372 B2* | 8/2014 | Klebuc ............... A61F 2/12  623/8 |
| 8,877,822 B2 | 11/2014 | Liu et al. |
| D723,162 S | 2/2015 | Brogan et al. |
| 9,011,333 B2 | 4/2015 | Geissler et al. |
| 9,044,897 B2 | 6/2015 | Manesis et al. |
| 9,050,184 B2 | 6/2015 | Van Epps |
| 9,138,311 B2* | 9/2015 | Van Epps ............... A61F 2/12 |
| 9,155,613 B2 | 10/2015 | Thompson et al. |
| 9,205,238 B2 | 12/2015 | Ledergerber |
| 9,205,577 B2 | 12/2015 | Liu et al. |
| 9,539,086 B2* | 1/2017 | Schuessler ............... A61L 27/56 |
| 9,593,224 B2 | 3/2017 | Liu et al. |
| 9,673,516 B2 | 6/2017 | Mejia |
| 9,688,006 B2 | 6/2017 | Nieto et al. |
| 9,750,600 B2 | 9/2017 | Mayo |
| 9,901,438 B2 | 2/2018 | Mejia et al. |
| 10,111,744 B2 | 10/2018 | Mora et al. |
| 10,176,412 B2 | 1/2019 | Geissler et al. |
| 10,376,360 B2* | 8/2019 | Bruchman ............... A61F 2/2415 |
| 2001/0010024 A1 | 7/2001 | Ledergerber |
| 2002/0038147 A1 | 3/2002 | Miller |
| 2002/0062154 A1 | 5/2002 | Ayers |
| 2002/0143396 A1 | 10/2002 | Falcon et al. |
| 2002/0193885 A1 | 12/2002 | Legeay et al. |
| 2003/0036803 A1 | 2/2003 | McGhan |
| 2003/0093151 A1 | 5/2003 | Zhang |
| 2003/0105469 A1 | 6/2003 | Karmon |
| 2003/0129717 A1 | 7/2003 | Becker et al. |
| 2003/0205846 A1 | 11/2003 | Bellin et al. |
| 2003/0208269 A1 | 11/2003 | Eaton |
| 2004/0010225 A1 | 1/2004 | Schuessler |
| 2004/0115241 A1 | 6/2004 | Calhoun et al. |
| 2004/0127985 A1 | 7/2004 | Bellin et al. |
| 2004/0137032 A1 | 7/2004 | Wang |
| 2004/0143327 A1 | 7/2004 | Ku |
| 2004/0148024 A1 | 7/2004 | Williams |
| 2004/0153151 A1 | 8/2004 | de Vicente |
| 2004/0176493 A1 | 9/2004 | Ferguson |
| 2004/0213986 A1 | 10/2004 | Kim et al. |
| 2005/0055093 A1 | 3/2005 | Brennan |
| 2005/0070124 A1 | 3/2005 | Miller et al. |
| 2005/0112169 A1 | 5/2005 | Brauker et al. |
| 2005/0122169 A1 | 6/2005 | Watanabe |
| 2005/0175702 A1 | 8/2005 | Muller-Schulte |
| 2005/0196452 A1 | 9/2005 | Boyan et al. |
| 2005/0216094 A1 | 9/2005 | Prewett |
| 2005/0251083 A1 | 11/2005 | Carr-Brendel et al. |
| 2006/0002810 A1 | 1/2006 | Grohowski |
| 2006/0036266 A1 | 2/2006 | Sulamanidze et al. |
| 2006/0036320 A1 | 2/2006 | Job |
| 2006/0136056 A1 | 6/2006 | Wohl |
| 2006/0224239 A1 | 10/2006 | Tiahrt |
| 2006/0229721 A1 | 10/2006 | Ku |
| 2006/0235094 A1 | 10/2006 | Habibi-Naini |
| 2006/0246121 A1 | 11/2006 | Ma |
| 2006/0257377 A1 | 11/2006 | Atala et al. |
| 2007/0038310 A1 | 2/2007 | Guetty |
| 2007/0093911 A1 | 4/2007 | Fricke et al. |
| 2007/0104693 A1 | 5/2007 | Quijano et al. |
| 2007/0104695 A1 | 5/2007 | Quijano et al. |

(56) References Cited

U.S. PATENT DOCUMENTS

| | | |
|---|---|---|
| 2007/0116735 A1 | 5/2007 | Calhoun et al. |
| 2007/0135916 A1 | 6/2007 | Maxwell et al. |
| 2007/0154525 A1 | 7/2007 | Calhoun et al. |
| 2007/0190108 A1 | 8/2007 | Datta et al. |
| 2007/0198085 A1 | 8/2007 | Benslimane |
| 2008/0009830 A1 | 1/2008 | Fujimoto et al. |
| 2008/0071371 A1 | 3/2008 | Elshout |
| 2008/0075752 A1 | 3/2008 | Ratner et al. |
| 2008/0095823 A1 | 4/2008 | Williams et al. |
| 2008/0154366 A1 | 6/2008 | Frank |
| 2008/0208336 A1* | 8/2008 | Job .................. A61F 2/12 623/8 |
| 2008/0241212 A1 | 10/2008 | Moses et al. |
| 2008/0268019 A1 | 10/2008 | Badylak et al. |
| 2008/0312739 A1 | 12/2008 | Agerup et al. |
| 2009/0045166 A1 | 2/2009 | Li |
| 2009/0082864 A1 | 3/2009 | Chen et al. |
| 2009/0087641 A1 | 4/2009 | Favis et al. |
| 2009/0093878 A1 | 4/2009 | Glicksman |
| 2009/0118829 A1 | 5/2009 | Powell et al. |
| 2009/0125107 A1 | 5/2009 | Maxwell |
| 2009/0148829 A1 | 6/2009 | Ecker et al. |
| 2009/0169716 A1 | 7/2009 | Linhardt et al. |
| 2009/0198331 A1 | 8/2009 | Kesten et al. |
| 2009/0198332 A1 | 8/2009 | Becker |
| 2009/0198333 A1 | 8/2009 | Becker |
| 2009/0254179 A1 | 10/2009 | Burnett |
| 2010/0042211 A1 | 2/2010 | Van Epps et al. |
| 2010/0075056 A1 | 3/2010 | Axisa et al. |
| 2010/0178414 A1* | 7/2010 | Judge ................ A61F 2/12 427/2.24 |
| 2010/0292790 A1 | 11/2010 | Stroumpoulis et al. |
| 2011/0035004 A1 | 2/2011 | Maxwell |
| 2011/0054605 A1 | 3/2011 | Becker |
| 2011/0093069 A1 | 4/2011 | Goraltchouk et al. |
| 2011/0106249 A1 | 5/2011 | Becker |
| 2011/0117267 A1 | 5/2011 | Powell et al. |
| 2011/0172798 A1 | 7/2011 | Staiger |
| 2011/0184531 A1 | 7/2011 | Goraltchouk et al. |
| 2011/0196488 A1 | 8/2011 | Goraltchouk et al. |
| 2011/0196489 A1 | 8/2011 | Van Epps et al. |
| 2011/0257623 A1 | 10/2011 | Marshall et al. |
| 2011/0276133 A1 | 11/2011 | Liu et al. |
| 2011/0276134 A1 | 11/2011 | Manesis et al. |
| 2011/0278755 A1 | 11/2011 | Liu et al. |
| 2011/0282444 A1 | 11/2011 | Liu et al. |
| 2011/0309541 A1 | 12/2011 | Thompson et al. |
| 2011/0313073 A1 | 12/2011 | Goraltchouk et al. |
| 2012/0004722 A1 | 1/2012 | Goraltchouk et al. |
| 2012/0041555 A1 | 2/2012 | Manesis et al. |
| 2012/0077010 A1 | 3/2012 | Manesis et al. |
| 2012/0077012 A1 | 3/2012 | Liu et al. |
| 2012/0077891 A1 | 3/2012 | Liu et al. |
| 2012/0101574 A1 | 4/2012 | Goraltchouk et al. |
| 2012/0142798 A1 | 6/2012 | Thompson et al. |
| 2012/0165934 A1 | 6/2012 | Schuessler |
| 2012/0185041 A1 | 7/2012 | Mortarino et al. |
| 2012/0221105 A1 | 8/2012 | Altman et al. |
| 2012/0232652 A1 | 9/2012 | Mora et al. |
| 2012/0245685 A1 | 9/2012 | Yu |
| 2012/0277858 A1 | 11/2012 | Brinon |
| 2012/0321777 A1 | 12/2012 | Stroumpoulis et al. |
| 2013/0013062 A1 | 1/2013 | Thompson et al. |
| 2013/0023987 A1 | 1/2013 | Liu et al. |
| 2013/0032962 A1 | 2/2013 | Liu et al. |
| 2013/0034633 A1 | 2/2013 | von Hassein |
| 2013/0053956 A1 | 2/2013 | Powell et al. |
| 2013/0158657 A1 | 6/2013 | Nofrey et al. |
| 2013/0178699 A1 | 7/2013 | Saint et al. |
| 2013/0209661 A1 | 8/2013 | Goraltchouk et al. |
| 2013/0245148 A1 | 9/2013 | Thompson et al. |
| 2013/0261745 A1 | 10/2013 | Van Epps |
| 2013/0295379 A1 | 11/2013 | Goraltchouk et al. |
| 2013/0302511 A1 | 11/2013 | Goraltchouk et al. |
| 2013/0310934 A1 | 11/2013 | Van Epps et al. |
| 2014/0005783 A1 | 1/2014 | Van Epps et al. |
| 2014/0039617 A1 | 2/2014 | Maxwell |
| 2014/0180412 A1 | 6/2014 | Nieto et al. |
| 2015/0282926 A1 | 10/2015 | Chacon et al. |
| 2016/0022866 A1 | 1/2016 | Liu et al. |
| 2016/0130690 A1 | 5/2016 | Winn et al. |
| 2016/0151542 A1 | 6/2016 | Liu et al. |
| 2017/0049549 A1 | 2/2017 | Bayat et al. |
| 2017/0256850 A1 | 9/2017 | Mejia |
| 2017/0290652 A1 | 10/2017 | Nieto et al. |
| 2018/0092726 A1 | 4/2018 | Van Epps et al. |
| 2018/0200043 A1 | 7/2018 | Mejia et al. |
| 2018/0360594 A1 | 12/2018 | Schuessler et al. |
| 2019/0029807 A1 | 1/2019 | Nieto et al. |

FOREIGN PATENT DOCUMENTS

| | | |
|---|---|---|
| CA | 2975348 | 8/2015 |
| CA | 3007138 | 6/2017 |
| CA | 3013698 | 8/2017 |
| CA | 3019747 | 10/2017 |
| CA | 3020876 | 10/2017 |
| CA | 3023507 | 11/2017 |
| CN | 2587376 Y | 11/2003 |
| CN | 104837441 | 8/2015 |
| CN | 108697337 | 10/2018 |
| CN | 109069251 | 12/2018 |
| CN | 109152531 | 1/2019 |
| CN | 109152640 | 1/2019 |
| EP | 0230672 A1 | 8/1987 |
| EP | 0293256 A1 | 11/1988 |
| EP | 0315814 A2 | 5/1989 |
| EP | 0332371 | 9/1989 |
| EP | 0419134 | 3/1991 |
| EP | 0522585 A1 | 1/1993 |
| EP | 0710468 | 5/1996 |
| EP | 1532942 A1 | 5/2005 |
| EP | 1796595 | 6/2007 |
| EP | 1847369 B1 | 12/2008 |
| EP | 2446858 | 5/2012 |
| EP | 2568875 | 3/2013 |
| EP | 2895994 | 7/2015 |
| EP | 2921137 | 9/2015 |
| EP | 2931490 | 10/2015 |
| EP | 2962662 | 1/2016 |
| EP | 3107487 | 12/2016 |
| EP | 3383314 | 10/2018 |
| EP | 3413788 | 12/2018 |
| EP | 2895109 B1 | 1/2019 |
| EP | 3439543 | 2/2019 |
| EP | 3442468 | 2/2019 |
| EP | 3443933 | 2/2019 |
| EP | 2227175 B1 | 3/2019 |
| ES | 2409691 | 6/2013 |
| FR | 2840617 A1 | 12/2003 |
| GB | 1022736 | 3/1966 |
| GB | 2225016 | 5/1990 |
| JP | 2003-062062 | 4/2003 |
| JP | 2007-029717 | 8/2007 |
| KR | 20180103873 | 9/2018 |
| KR | 20180116302 | 10/2018 |
| KR | 20180134358 | 12/2018 |
| KR | 20180137503 | 12/2018 |
| KR | 20190008252 | 1/2019 |
| MX | 2012012801 A | 5/2014 |
| RU | 2340308 C1 | 12/2008 |
| WO | WO 90/14927 A1 | 12/1990 |
| WO | WO 97/15242 | 5/1997 |
| WO | 1998010803 A1 | 3/1998 |
| WO | WO 98/42318 | 10/1998 |
| WO | 2000024437 A2 | 5/2000 |
| WO | WO 00/56376 | 9/2000 |
| WO | 2004037318 A2 | 5/2004 |
| WO | 2004062531 A1 | 7/2004 |
| WO | WO 2005/020849 | 3/2005 |
| WO | 2006133366 A1 | 12/2006 |
| WO | WO 2008/001591 | 1/2008 |
| WO | 2009061672 A1 | 5/2009 |
| WO | 2009110917 A1 | 9/2009 |

(56) References Cited

FOREIGN PATENT DOCUMENTS

| WO | 2010019292 A1 | 2/2010 |
| WO | 2010019761 A1 | 2/2010 |
| WO | 2010136840 A2 | 12/2010 |
| WO | WO 2011/066441 | 6/2011 |
| WO | 2011094155 A2 | 8/2011 |
| WO | 2011097499 A1 | 8/2011 |
| WO | WO 2011/143324 | 11/2011 |
| WO | 20130184569 A1 | 12/2013 |
| WO | WO 2014/043631 | 3/2014 |
| WO | WO 2014/047013 | 3/2014 |
| WO | WO 2014/076339 | 5/2014 |
| WO | WO 2015/121686 | 8/2015 |
| WO | WO 2017/093528 | 6/2017 |
| WO | WO 2017/137853 | 7/2017 |
| WO | WO 2017/175055 | 10/2017 |
| WO | WO 2017/181144 | 10/2017 |
| WO | WO 2017/184962 | 10/2017 |
| WO | WO 2017/196973 | 11/2017 |
| WO | WO 2018/078446 | 5/2018 |
| WO | WO 2018/188930 | 10/2018 |

OTHER PUBLICATIONS

Barnsley, Philip et al., Textured Surface Breast Implants in the Prevention of Capsular Contracture Among Breast Augmentation Patients: A Meta-Analysis of Randomized Controlled Trials, Plastic and Reconstructive Surgery, 2006, 2182-2190, 117(7).

Barr, S. et al., Current Implant Surface Technology: An Examination of Their Nanostructure and Their Influence on Fibroblast Alignment and Biocompatibility, Elastic, 2009, 198-217, 9.

Brauker, James et al., Neovascularization of Synthetic Membranes Directed by Membrane Microarchitecture, Journal of Biomedical Materials Research, 1995, 1517-1524, 29, John Wiley & Sons, Inc.

Brohim, Robert et al., Early Tissue Reaction to Textured Breast Implant Surfaces, Annals of Plastic Surgery, Apr. 1992, 354-362, vol. 28, No. 4.

Inamed Aesthetics Brochure, Silicone-Filled Breast Implants, Directions for Use Style 410, 2003, 23 pages, www.inamedaesthetics.com.

Ma, Peter, Scaffolds for Tissue Fabrication, Materials Today, 2004, 30-40, 7.

Mikos, Antonius et al., Formation of Highly Porous Biodegradable Scaffolds for Tissue Engineering, Electronic Journal of Biotechnology, 2000, 114-119, 3(2).

Minami, Eliza, The Composition and Behavior of Capsules Around Smooth and Textured Breast Implants in Pigs, Plast. Reconstr. Surg., 2006, 874-884, 118.

Murphy, William L. et al., Salt Fusion: An Approach to Improve Pore Interconnectivity Within Tissue Engineering Scaffolds, Tissue Engineering, 2002, 43-52, 8 (1), US.

Sharkawy, Adam et al., Engineering the Tissue Which Encapsulates Subcutaneous Implants. II. Plasma-Tissue Exchange Properties, Journal of Biomedical Materials Research, 1998, 586-597, 40, John Wiley & Sons, Inc.

Wei, Guobao et al., Macroporous and Nanofibrous Polymer Scaffolds and Polymer/Bone-Like Apatite Composite Scaffolds Generated by Sugar Spheres, Journal of Biomedical Materials Research, 2006, 306-315, 78A.

Zhang, et al., Macroporous Alumina Monoliths Prepared by Filling Polymer Foams with Alumina Hydrogels, Journal of Materials Science, 2009, 931-938, 44, Springer Science.

Capes et al., "Fabrication of polymeric scaffolds with a controlled distribution of pores," J of Materials Science: Materials in Medicine, Dec. 2005, vol. 16, No. 12, DD 1069-1075.

Kim et al., "Modified release of coated sugar spheres using drug-containing polymeric dispersions," Archives Pharmacal Research, 2007, vol. 30, No. 1, pp. 124-130.

Yu et al., "Softness measurement for open-cell foam materials and human soft tissue," Measurement Science and Technology, 2006, vol. 17, pp. 1785-1791.

\* cited by examiner

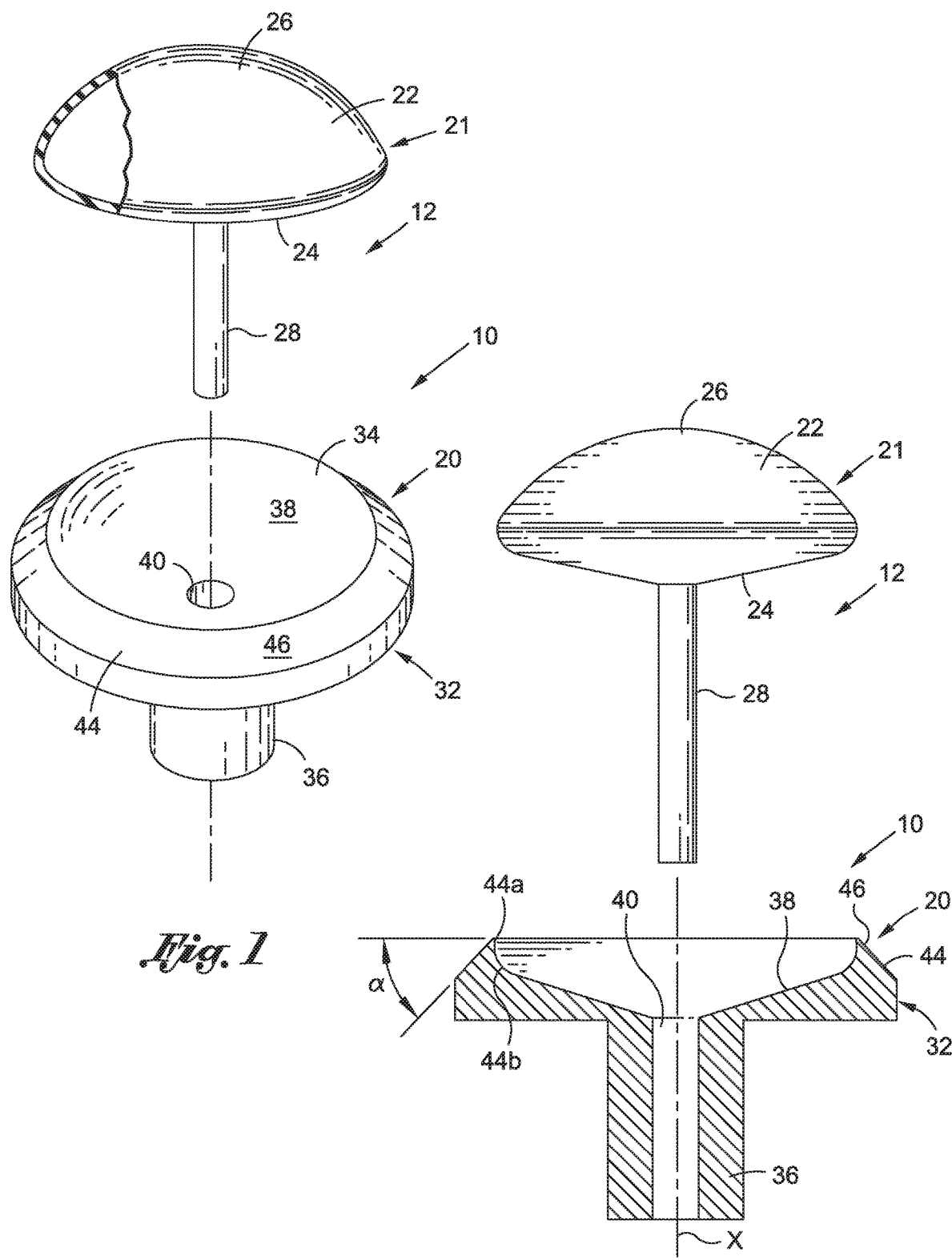

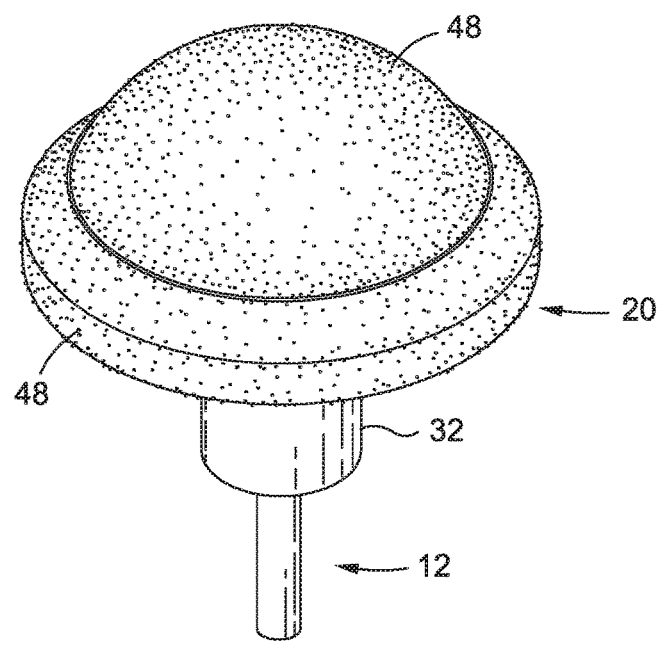
Fig. 3
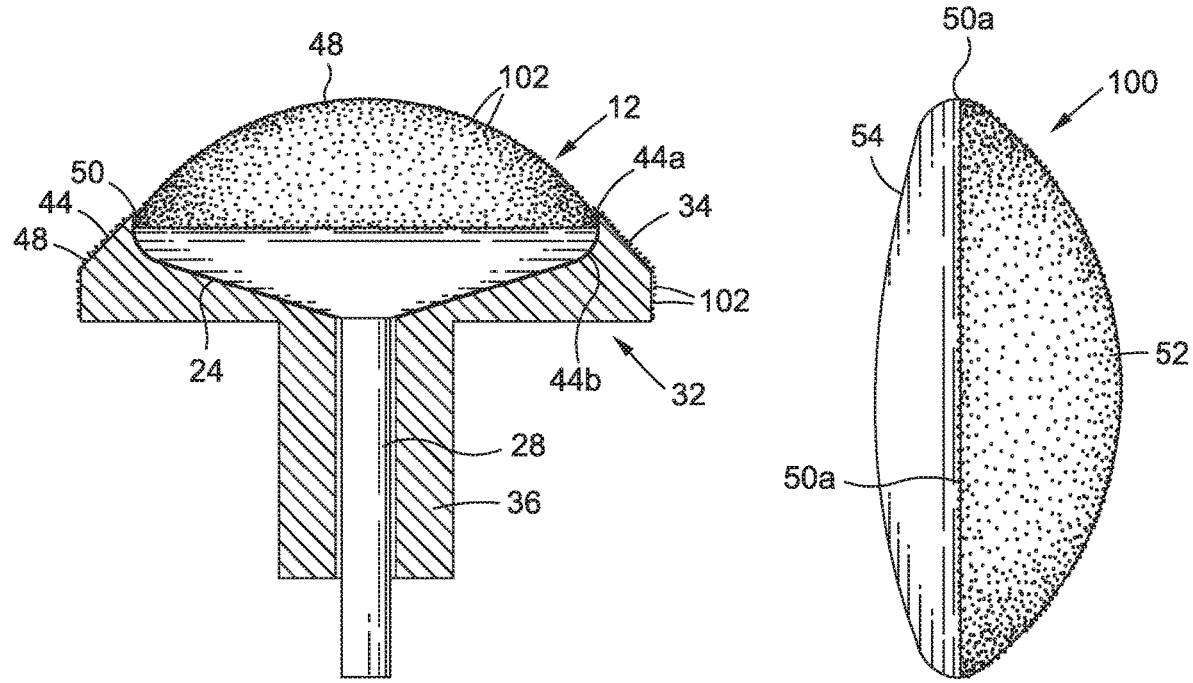
Fig. 4
Fig. 5

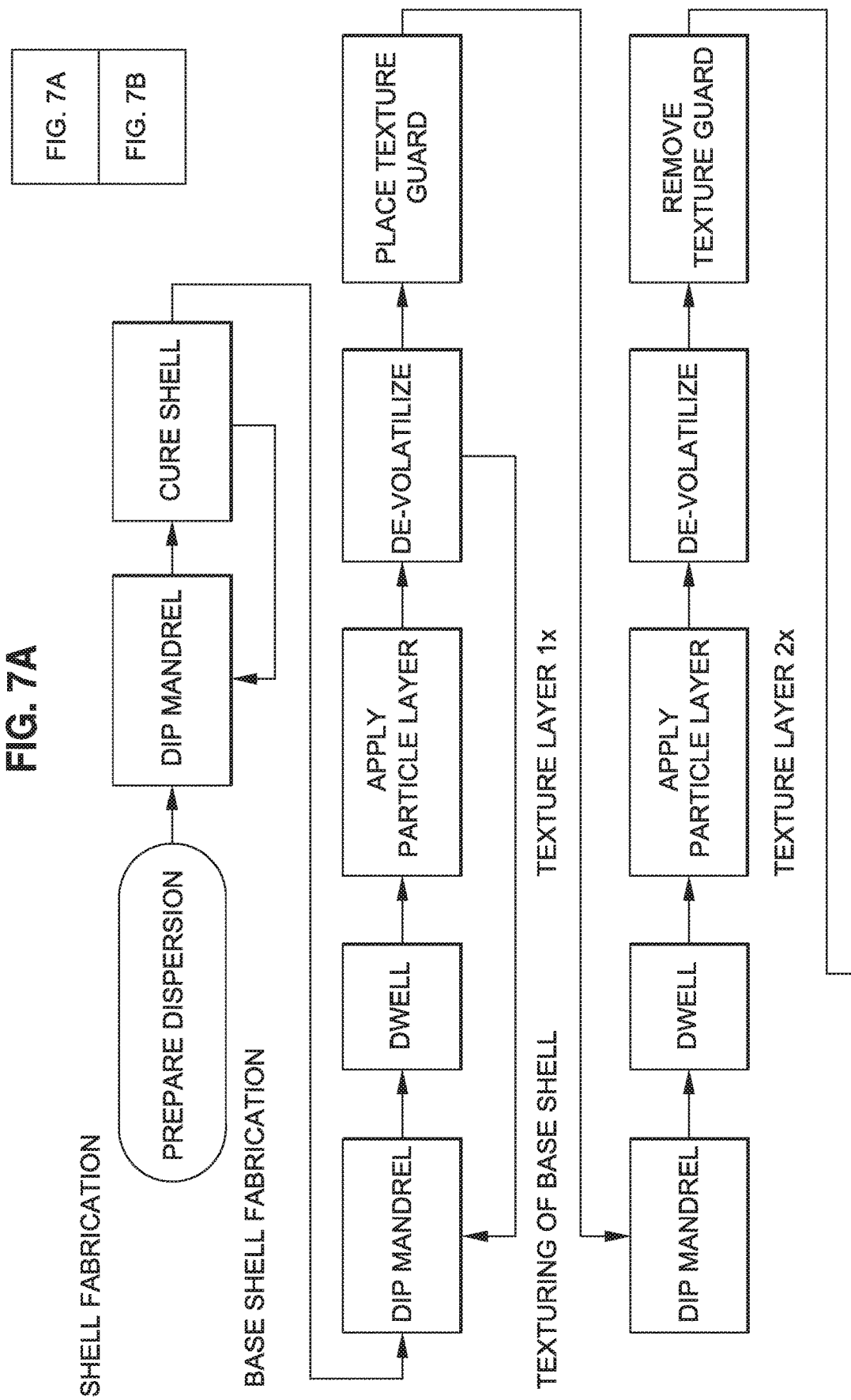

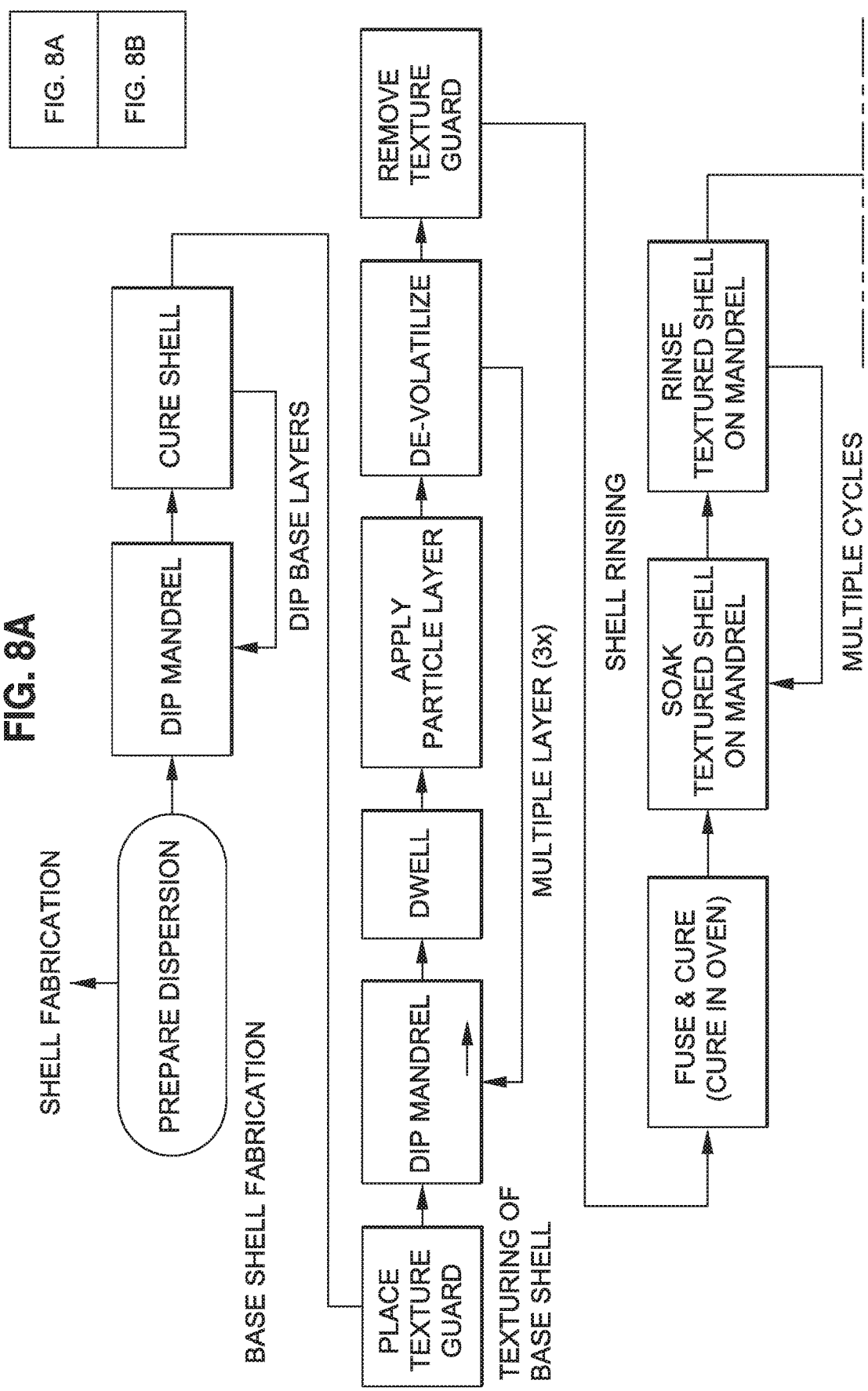

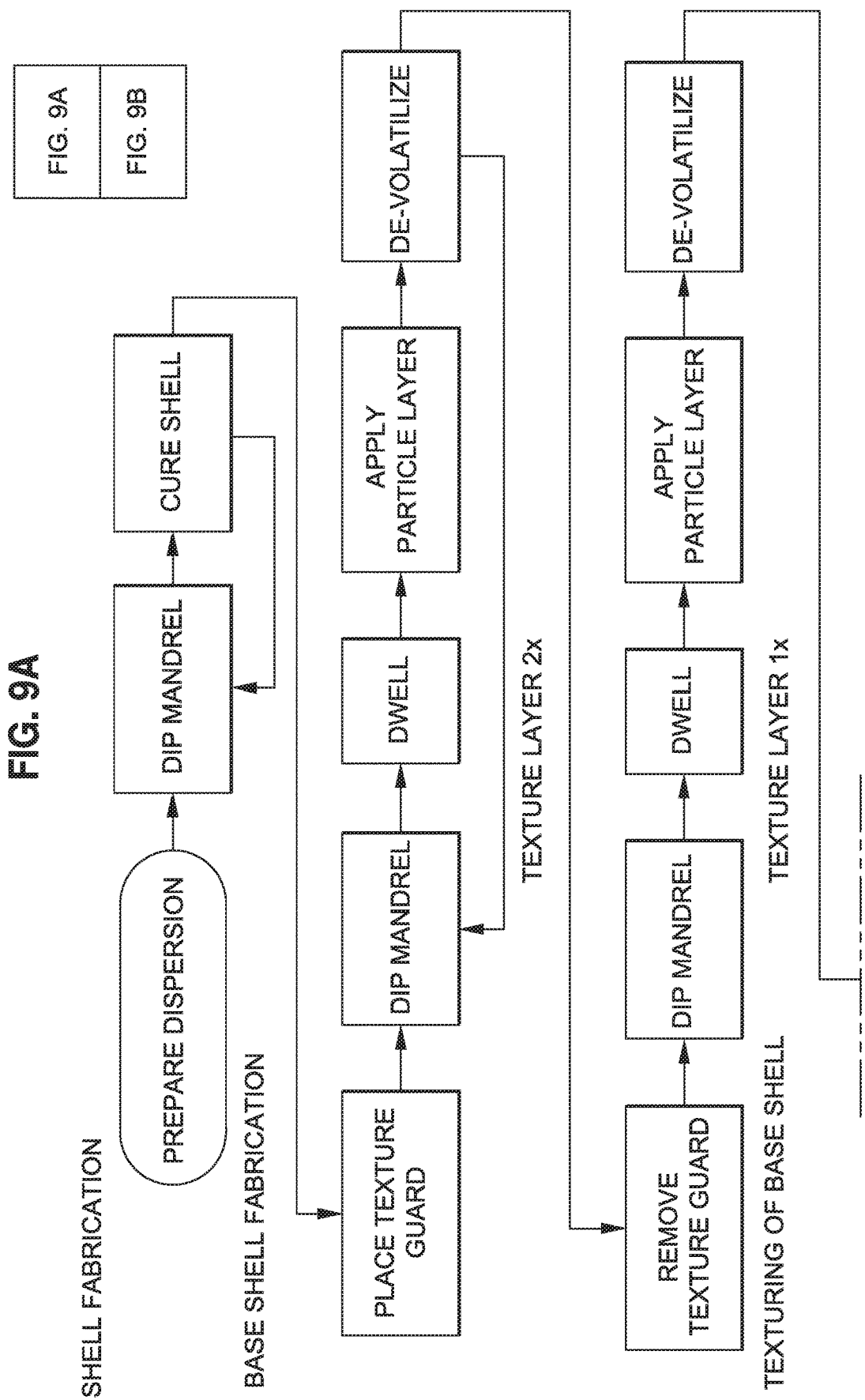

DEVICE AND METHOD FOR MAKING A VARIABLE SURFACE BREAST IMPLANT

This application is a continuation of copending U.S. patent application Ser. No. 14/106,524 which claims priority and the benefit of U.S. Provisional Patent Application No. 61/736,687, filed Dec. 13, 2012, the entire disclosure of which is incorporated herein by this reference.

The present invention generally relates to breast implant technology and more specifically relates to devices and methods for making a variable surface breast implant.

BACKGROUND

Soft tissue implants are commonly used for a wide variety of clinical and cosmetic purposes. One use involves reconstructive applications that rebuild and restore a body part or structure to correct deformities from congenital anomalies, trauma, cancer, infections, disease, or medication side effects. The soft tissue implant serves to replace lost tissue, provide aesthetic improvement, support surrounding tissue and/or to maintain the normal appearance of the body. The restoration of a normal appearance has a significant beneficial psychological effect on post-operative patients, alleviating much of the shock and depression that often follows extensive surgical procedures, Another use involves augmentation applications that alter a body part or structure usually to improve its cosmetic or aesthetic appearance. Augmentation of the appearance also has beneficial psychological effects that improve self-esteem, well-being, and confidence of an individual.

The use of implantable prosthesis for breast shaping, for example, for breast reconstruction following traumatic or surgical loss of breast tissue or, electively to increase volume of the breast is well known. Typically, the prosthesis or implant comprises of a soft, flexible envelope containing a liquid or gelatinous material. The envelope is commonly made from silicone or other bio-compatible polymer with varying degrees of elastic memory and permeability. These prostheses are filled with saline, and silicone oil or gel to mimic the tone and feel of natural breast tissue.

Capsular contracture is an adverse event related to breast implant surgery. It is believed to be a result of the immune system response to the presence of a foreign material in the body. A normal response of the body to the presence of a newly implanted object, for example a breast implant, is to form periprosthetic tissue, sometimes in the form of a capsule containing collagen fibers around the implant. Capsular contracture occurs when the capsule begins to contract and constrict the implant. This contracture can be discomforting or even extremely painful, and can cause distortion of the appearance of the augmented or reconstructed breast.

The exact cause of contracture is not known. However, some factors that may influence contracture include bacterial contamination of the implant prior to placement, submuscular versus subglandular placement, and smooth surface implants versus textured surface implants, the type or degree of texture on the implant surface, and bleeding or trauma to the area.

Surface texturing has been shown to reduce capsular contracture when implants are placed in the subglandular position compared to what are known as "smooth" surface implants. In other words, it is generally well known in the art that patients fitted with textured implants are less likely to exhibit contracture, relative to patients fitted with non-textured or smooth surface implants placed subglandularly. However, there is still a need for a textured implant that is specifically designed to encourage optimal tissue integration in the most beneficial location, and potentially reduce capsule formation and collagen fiber alignment described herein.

Conventional manufacturing processes for textured implants include the application of dissolvable particles onto a tacky elastomeric surface of an implant shell and subsequent removal thereof, leaving a dimpled or textured surface in the elastomer. Alternating layers of particles and elastomer provide a way to produce a textured surface defined by a porous surface having a desired depth.

There remains a need for better devices and methods for texturing outer surfaces of breast implants.

SUMMARY

Accordingly, devices and methods for making textured breast implants are provided. The devices and methods are more specifically directed to implants with variable surfaces, including textured surfaces.

The present invention provides method for making prostheses, or soft tissue implants, for example, implants suitable for use in reconstruction or augmentation of the human breast. Breast implants made in accordance with the methods and devices described herein, generally comprise a soft elastomeric exterior and a gel or saline core or filling. The exterior has a variable texture for enhancing adhesion of tissue in desired regions of the implant.

In one aspect, methods are provided for texturing a breast implant exterior surface. The exterior of a breast implant can be generally defined by a posterior surface which generally faces the chest wall, and an anterior surface which faces away from the chest wall and when the implant is implanted in a breast. Conventionally, both the anterior surface and the posterior surface are identical to each other in terms of surface texture or lack thereof. In accordance with one aspect of the invention, the devices and methods are useful for making a breast implant having an a posterior surface and an anterior surface that are different from one another, for example, have different textures from one another, or have texture on one surface and relative lack of texture on another surface.

In another aspect, a device for use in molding a variable textured breast implant is provided. The device generally comprises a member structured to engage a breast implant mandrel having a molding surface and a stem depending therefrom. The member includes a base-engaging distal portion and a stem-engaging proximal portion depending from the base-engaging distal portion. The base-engaging distal portion comprises a base-engaging surface, and an aperture defined in the base-engaging surface for receiving the stem of the mandrel when the mandrel is seated in the base engaging portion. The member is made of a material and is structured such that, when coupled with a breast implant mandrel, it provides a barrier for preventing silicone dispersion and/or texturing particles from contacting a portion of the mandrel when the mandrel is immersed in a silicone dispersion and/or texturing particles. In one embodiment, the member includes a proximally sloping rim circumscribing the base-engaging surface. The member may be made of any suitable material, for example, but not limited to an elastomeric material such as a silicone elastomer, or alternatively, a relatively rigid polymeric material, such as Acetal.

In one aspect the base-engaging surface of the member is configured or shaped to conform to a base region of breast implant mandrel. In one embodiment, the base-engaging surface is a substantially conically shaped surface. The aperture may be disposed generally in the center of the conically shaped surface.

In one embodiment, the proximally sloping rim slopes at an angle substantially equal to a slope of the mandrel surface, such that the proximally sloping rim substantially aligns with the mandrel surface when the mandrel is seated in the base-engaging portion.

In some embodiments, the proximally sloping surface has a slope angle relative to a plane perpendicular to the longitudinal axis of the member, the slope angle being between about 20 degrees and about 70 degrees, for example, between about 30 degrees and about 60 degrees. In one embodiment, the slope angle is about 45 degrees.

In another aspect of the invention, a breast prosthesis shell is provided that includes a surface that has been textured using the device described herein.

In yet another aspect of the invention, a method for making a textured breast implant is provided, the method comprising the steps of securing the device described elsewhere herein to a breast implant mandrel coated with a tacky elastomer, contacting the tacky elastomer with texturing particles, for example, by immersing the breast implant mandrel and device secured thereto into a bath of texturing particles; removing the device from the mandrel; curing the tacky elastomer; and removing the texturing particles to obtain a breast implant shell having a first textured surface and a second surface, for example a smooth surface, different from the first textured surface.

In one aspect of the invention, a breast implant is provided, the implant comprising an elastomeric envelope having a posterior surface defined by an cellular texture having a first depth defined by interconnected pores, the first depth being at least three pores in depth, and an anterior surface defined by a open cell texture having a second depth defined by pores, the second depth being about one pore in depth.

In yet another aspect of the invention, an assembly is provided for use in making a variable textured breast implant, the assembly comprising a mandrel having a molding surface and a stem depending therefrom and a device for receiving the mandrel as disclosed elsewhere herein.

Each and every feature described herein, and each and every combination of two or more of such features, is included within the scope of the present invention provided that the features included in such a combination are not mutually inconsistent.

BRIEF DESCRIPTION OF THE DRAWINGS

These and other aspects, features and advantages of the present invention may be more clearly understood with reference to the following Detailed Description when considered in conjunction with the accompanying Drawings, of which:

FIG. 1 is a perspective view of an assembly for use in making a variable textured breast implant;

FIG. 2 is a view similar to FIG. 1, with a portion of the assembly shown in cross-section;

FIG. 3 is a perspective view of the assembly shown in FIG. 1, as being used to form a variable textured breast implant shell;

FIG. 4 is a partial cross-sectional side view of the assembly as being used to form a variable textured breast implant shell, as shown in FIG. 3; and FIG. 5 is a side view of a breast implant formed with the assembly shown in FIG. 3;

FIGS. 7, 7A and 7B illustrate a method of the invention for producing a variable textured breast implant.

FIGS. 8, 8A and 8B illustrate another method of the invention for producing a variable textured breast implant.

FIGS. 9, 9A and 9B illustrate yet another method of the invention

DETAILED DESCRIPTION

Figure 6:
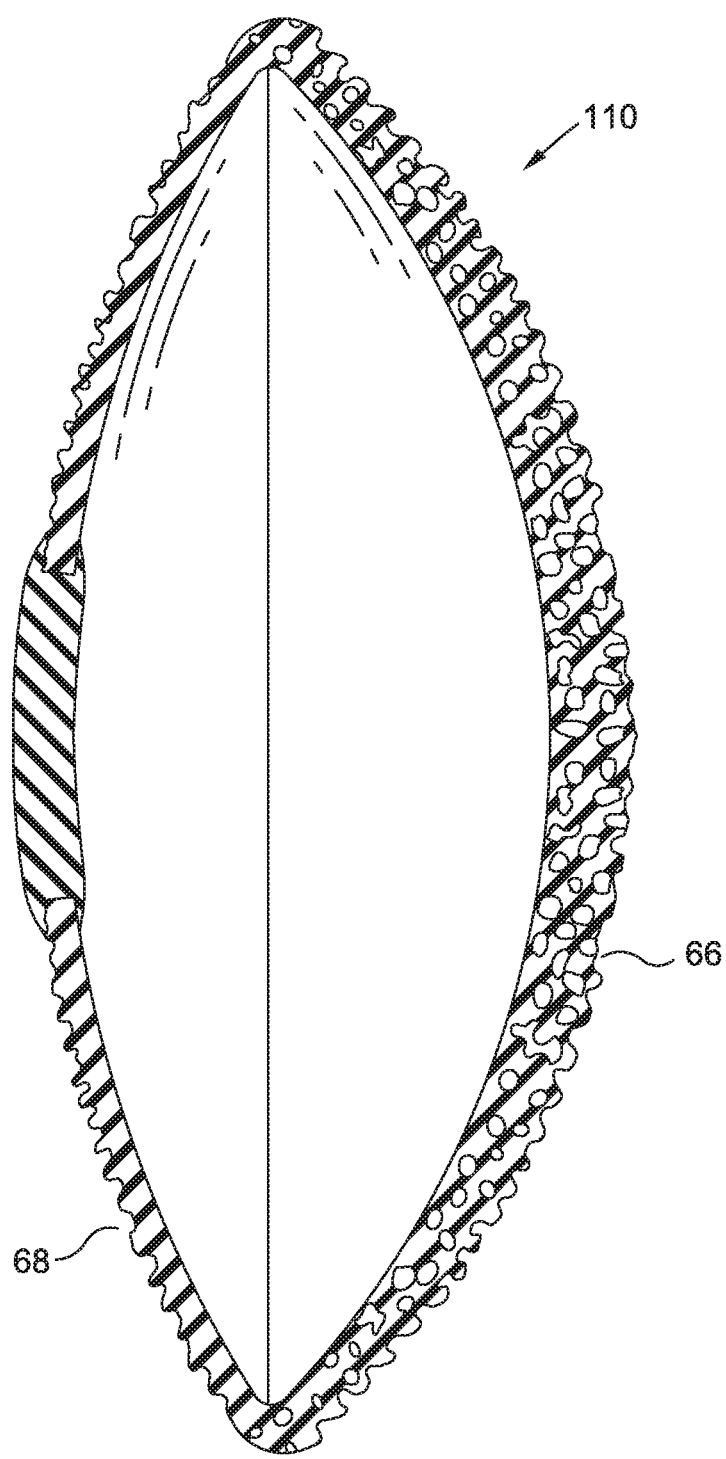
FIG. 6 is a cross sectional view of another implant formed with the assemblies, devices or methods of the invention.

Turning now to FIGS. 1 and 2, an assembly of the invention is shown generally at 10, and comprises a mandrel 12, and a device 20 for use in molding a variable textured breast implant when used in conjunction with the mandrel 12.

The mandrel 12 may similar or identical to a standard, conventional breast implant mandrel 12, generally including a shaped form 21 defining a molding surface 22 having a proximal region 24 and a distal region 26 which together define a configuration of a breast implant shell 100 (shown, for example, in FIG. 6) to be molded therefrom. The mandrel further includes a stem 28 secured to the form 21 and depending in a proximal direction, for enabling manipulation of the mandrel 12 during the molding process.

In the shown embodiment, device 20 comprises a member 32 structured to engage a breast implant mandrel, such as mandrel 12. Member 32 generally includes a base-engaging distal portion 34 and a stem-engaging proximal portion 36 depending from the base-engaging distal portion 34. The base-engaging distal portion 34 comprises a base-engaging surface 38, an aperture 40 defined in the base-engaging surface 38, and a rim 44 circumscribing the base-engaging surface 38. The base engaging surface 38 has a shape in conformance with portion of the shaped form 21, for example, is conically shaped as shown most clearly in FIGS. 1, 2 and 4.

Turning briefly as well to FIG. 4, the stem-engaging proximal portion 36 of member 32 is structured to receive the stem 28 of mandrel 12 when mandrel 12 is seated in the base-engaging portion 34. As shown in FIG. 4, member 32 provides a shield or barrier for preventing silicone dispersion and/or texturing particles from contacting or adhering to a portion of the mandrel 12, for example, mandrel proximal region 24, when the mandrel 12 is immersed in a silicone dispersion and/or texturing particles 102.

Member 32 is configured and structured to provide a compliant, mating seal between a silicone elastomer covered mandrel 12 and base-engaging surface 38. Turning back now to FIG. 2, rim 44 comprises a surface 46 which slopes in a proximal direction as shown, having a slope angle ($\alpha$) relative to a plane perpendicular to the longitudinal axis X of the member 32. The slope angle is between about 20 degrees and about 70 degrees, for example, between about 30 degrees and about 60 degrees. In one embodiment, the slope angle ($\alpha$) is about 45 degrees.

Turning specifically to FIG. 2, configuration of rim 44, having a sharp edge 44a and concave region 44b, may be configured to enhance sealing between member 32 and mandrel 12, for example, by providing a higher unit pressure against mandrel. The radius of curvature (R) of concave region 44b, in the shown embodiment, is about 0.34".

Slope angle $\alpha$ may function in part to facilitate effective draining of particles and prevent pooling of texture particles 102 along rim 44 during the texturing process described hereinafter. For example, the proximally sloping rim 44 slopes at an angle substantially equal to a slope of the mandrel surface, such that the proximally sloping rim substantially aligns with the mandrel surface when the mandrel is seated in the base-engaging portion, as shown most clearly in FIG. 4.

In one aspect of the invention, methods are provided for making a variable textured breast implant shell, for example, using the assembly 10 shown in FIGS. 1 and 2.

In one embodiment useful for making a breast implant 100 having a textured surface on one side thereof and a smooth or untextured surface on an opposing side thereof, such as shown in FIG. 5, the method may include providing a breast implant mandrel 12 having a cured silicone elastomer coating thereon, securing the device 20 to the mandrel 12, coating the breast implant mandrel with a tacky elastomer, such as a silicone dispersion, for example, by dipping, spraying or other suitable means, and immersing the breast implant mandrel 12 and device 32 secured thereto into a bath of texturing particles. Texturing particles may be any suitable texturing particles known in the art, for example, salt crystals, sugar crystals, starch beads, dissolvable polymeric beads, etc. Certain advantageous texturing particles useful with the present devices and methods are described in U.S. patent application Ser. No. 13/104,811 filed on May 21, 2012, and U.S. patent application Ser. No. 13/631,091, filed on Sep. 28, 2012, the entire content of each of these applications incorporated herein by this specific reference.

The assembly 10 at this point in the process is illustrated in FIGS. 3 and 4, which show mandrel 12 and member 32 having an elastomer particle-coated construction 48, as shown. The application of elastomer and particles can be repeated to achieve a desired thickness of texturing on the shell. The assembly 10 is then placed under curing conditions, for example, is placed into a curing chamber, for example, a heated oven, for a suitable amount of time, to cause at least partial curing of the elastomer coating. In this step, in some embodiments, the texturing particles may begin to melt and adhere to one another, which will provide an open cell, or interconnected cell texture when the particles are removed (see briefly, for example, FIG. 6).

Further, in some embodiments, the curing step is performed so that the elastomer is not fully cured at this point, but remains somewhat soft and/or tacky. This may be helpful to facilitate separation of the mandrel 12 from the member 32. Further still, optionally, a cutting implement may be used to sever the elastomer along a juncture 50 between the mandrel 12 and member 32, to produce a clean seam 50a between textured and untextured portions of the implant shell 100, for example, as shown in FIG. 5.

After the curing step, the texturing particles may then be removed from this construction 48 by any suitable means, for example, rinsing or dissolving in a solvent, leaving a textured porous surface. Member 32 is removed from the mandrel 12, for example, by sliding member 32 off of mandrel stem 28, and the elastomer/particle layered construction 48 is carefully stretched apart from and removed from the shaped form 21, resulting in a hollow, flexible envelope. In some embodiments, the particle removal step may be performed after the construction 48 is removed from the mandrel. Once the particles are removed from the elastomer, the construction 48 is useful as a breast implant shell 100 having one side, for example an anterior side 52 that textured with cavities remaining from the removed particles, and an opposing side, for example, a posterior side 54, that is smooth and untextured, such as shown in FIG. 5. Finishing steps that are conventional may be performed to seal the aperture left from the mandrel stem with a patch, for example, and the shell 100 may be filled with saline or gel in any conventional manner.

The present invention can be modified to achieve a number of different types of breast implant shells having different forms of variable texture. For example, in some embodiments, a breast implant shell 110, shown in FIG. 6, having a first textured surface 66 produced by multiple layers, for example, three or more layers of particles/elastomer, and a second textured surface 68 produced by relatively fewer layers, for example, one layer, of particles/elastomer, may be provided. This may be accomplished substantially as described elsewhere herein, with one difference being that member 32 may be installed on mandrel 12 when the mandrel already includes a particle/elastomer covered surface, for example, a single layer of particles on the entire implant surface including the portion covered by the member 32. After installing of the member 32, further layers of particles and elastomer may be layered onto the mandrel/member assembly, while the member 32 is in place providing a shield from elastomer and particle application on exposed portions.

The resulting shell 110, after removal of particles, is shown in cross-section in FIG. 6. In this embodiment, the first textured surface 66 defines the anterior surface of the shell, outwardly facing breast tissue when implanted, and the second textured surface 68 defines the posterior surface of the shell, rearwardly facing the chest wall.

Figure 7B:
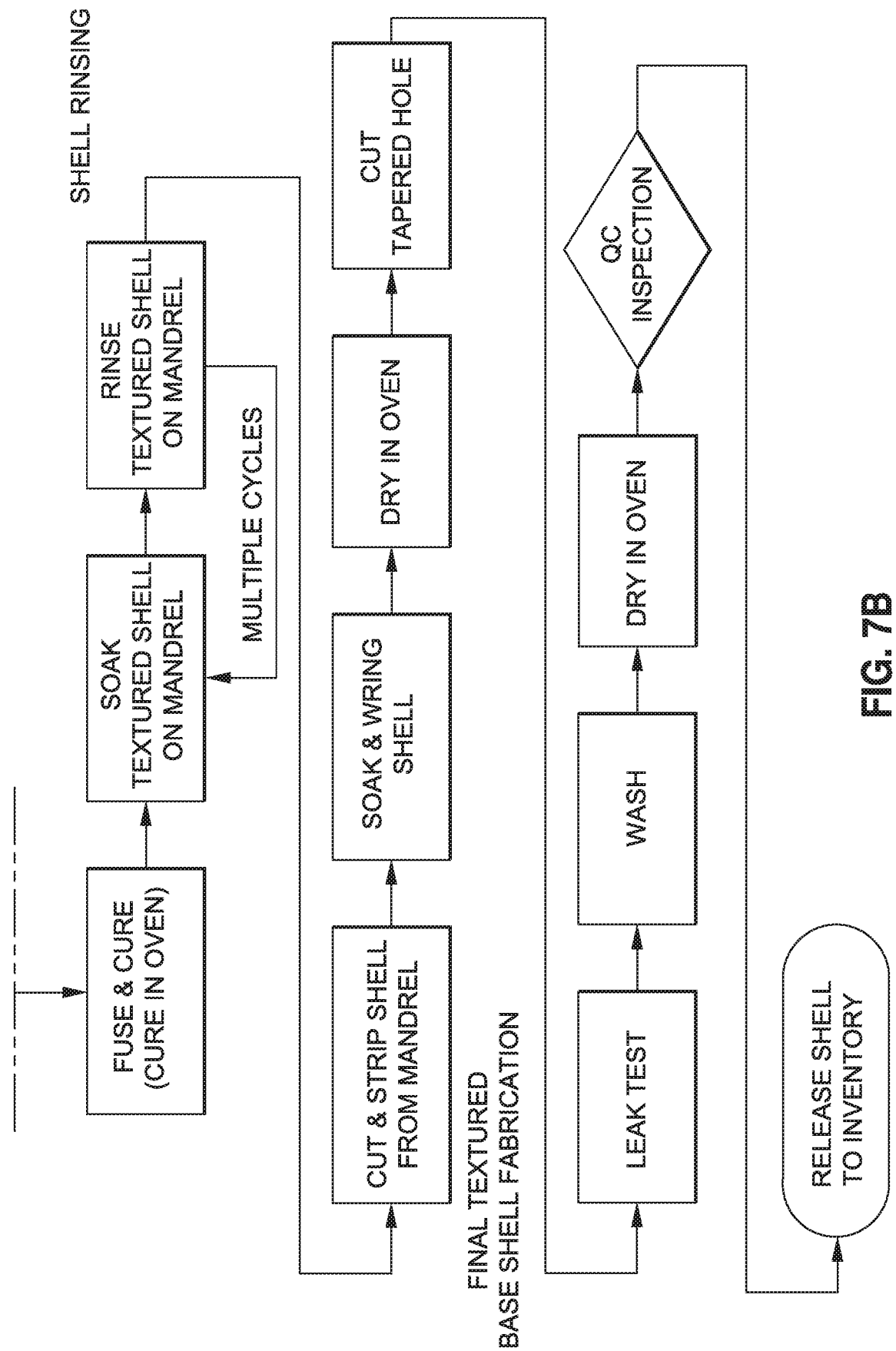
Figure 8B:
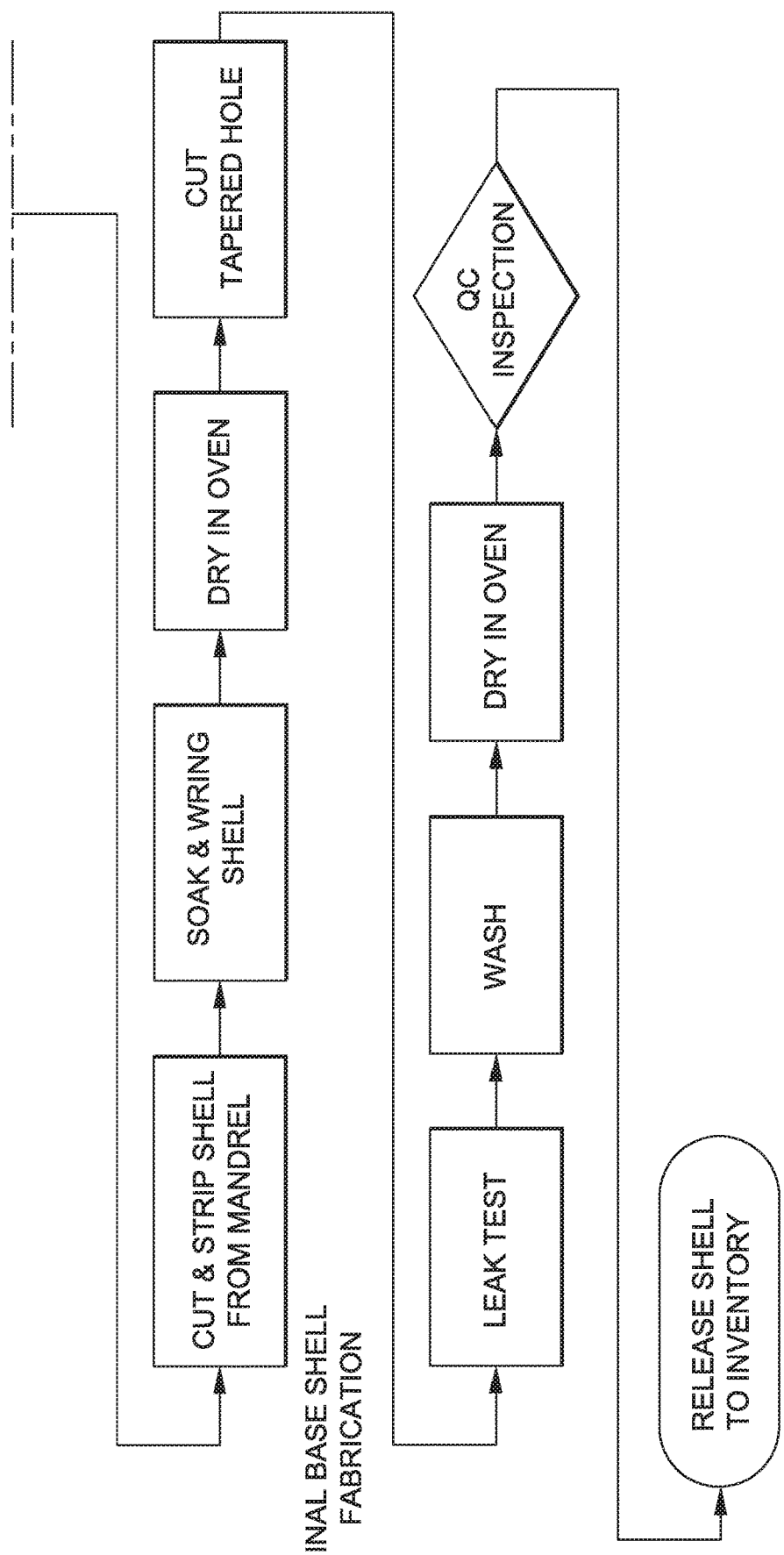
Figure 9B:
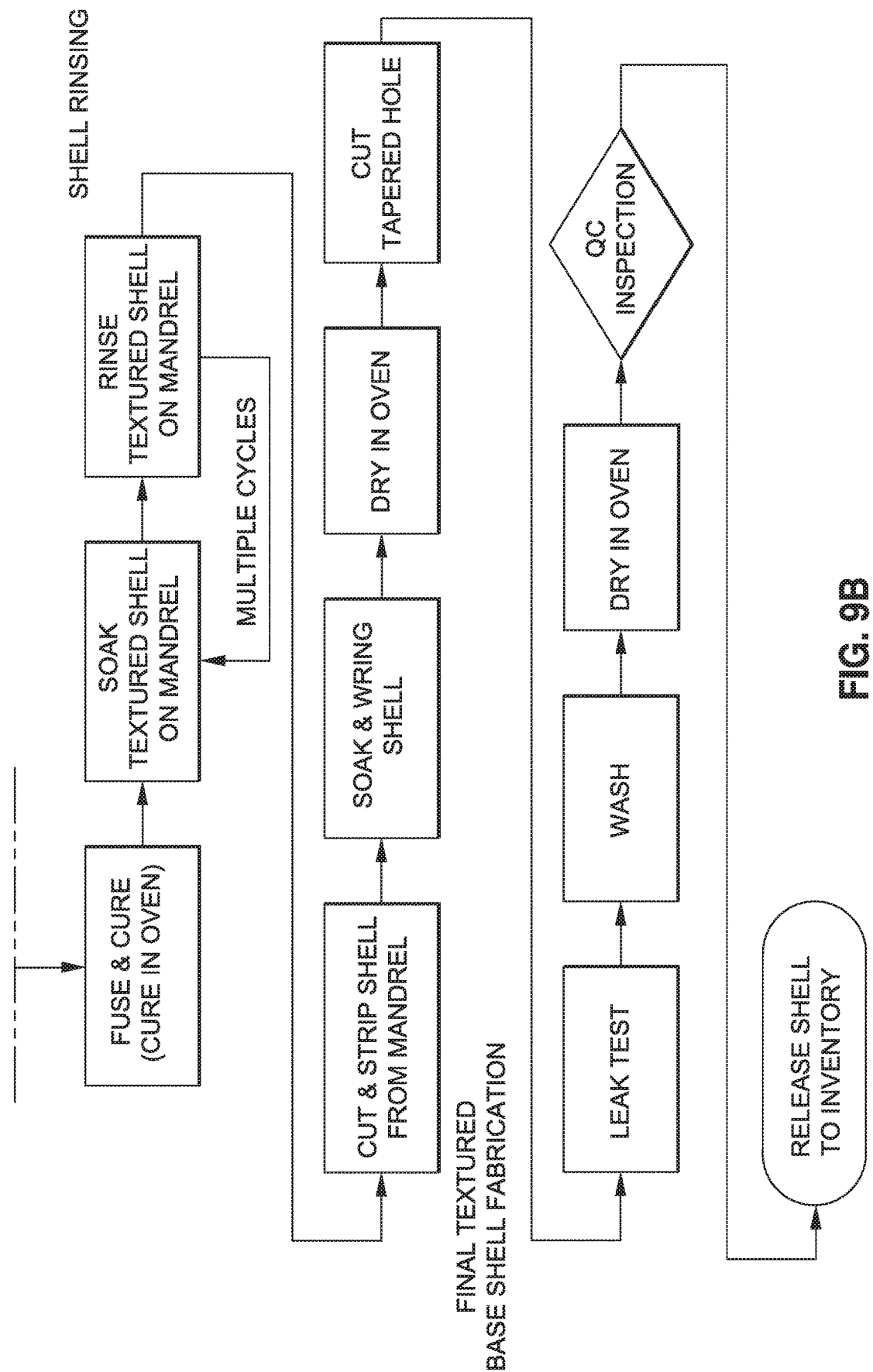

Other exemplary methods of the invention are shown as Flow Diagrams in FIGS. 7-9. The method shown in FIG. 7 (FIGS. 7a and 7B) can be used to create a breast implant shell having a single layered texture on one side of the implant, e.g. the posterior surface, and a double layered texture on another side of the implant, e.g. the anterior surface. The method shown in FIG. 8 (FIGS. 8a and 8B) can be used to create a breast implant shell, for example, shell 100, having a smooth surface on one side of the implant, e.g. the posterior surface, and a triple layer of texture on another surface, e.g. the anterior surface. The method shown in FIG. 9 (FIGS. 9a and 9B) can be used to create an implant shell having as single layer of texture on one surface and a double, triple, or greater number of layers of texture on an opposing surface, for example, such as implant 110 shown in FIG. 6.

In yet another aspect of the invention, a breast implant is provided having a variable textured surface. The implant may be manufactured using the assemblies, devices and methods disclosed herein. The implant generally comprises an anterior surface having a multilayered texture defined by open cell pores of a first depth, and a posterior surface having a single layered texture defined by open cell pores of a second depth that is less than the first depth. The implant can be made using the assemblies, devices and methods described herein.

Unless otherwise indicated or otherwise clearly contradicted by context, combinations of the above-described elements in all possible variations thereof are contemplated to be included within the scope of the invention.

What is claimed is:

1. A device for use in molding a variable textured breast implant, the device comprising:
   a breast implant mandrel having a stem depending therefrom; and
   a member structured to engage the breast implant mandrel, the member including a base-engaging distal portion and a stem-engaging proximal portion depending from the base-engaging distal portion, the base-engaging distal portion comprising a base-engaging surface, the base-engaging surface defining a mating seal between the mandrel as covered with a silicone elastomer and the base-engaging distal portion upon seating the mandrel in the base engaging distal portion, an aperture defined from the base-engaging surface through the member, and a proximally sloping rim circumscribing the base-engaging surface, the stem-engaging proximal portion structured to receive the stem of the mandrel seated in the base-engaging distal portion via the aperture, and the member providing a barrier for preventing a silicone dispersion and/or texturing particles from contacting a base portion of the seated mandrel when the mandrel is immersed in the silicone dispersion and/or texturing particles for adhering the dispersion and/or particles to an exposed portion of the covered, seated mandrel.

2. The device of claim 1 wherein the base-engaging surface has a shape conforming to a base of the breast implant mandrel.

3. The device of claim 1 wherein the base-engaging surface is a substantially conically shaped surface.

4. The device of claim 1 wherein the base-engaging surface is a substantially conically shaped surface and the aperture is disposed generally in the center of the conically shaped surface.

5. The device of claim 1 wherein the proximally sloping rim slopes at an angle substantially equal to a slope of the exposed portion such that the proximally sloping rim substantially aligns with the mandrel surface when the mandrel is seated in the base-engaging distal portion.

6. The device of claim 1 wherein the stem-engaging proximal portion defines a proximal portion cross-sectional profile and the base-engaging distal portion defines a distal portion cross-sectional profile, and the proximal portion cross-sectional profile is smaller than the distal portion cross-sectional profile.

7. An assembly useful for making a breast implant shell, the assembly comprising:

a mandrel having a molding surface and a stem depending therefrom;

a device comprising a member structured to receive a portion of the molding surface and the stem, the member including a base-engaging distal portion and a stem-engaging proximal portion depending from the base-engaging distal portion, the base-engaging distal portion comprising a base-engaging surface, the base-engaging surface defining a mating seal between the mandrel as provided with a particle-coated tacky surface and the base-engaging distal portion upon seating the mandrel in the base-engaging distal portion, an aperture defined from the base-engaging surface through the member, and a proximally sloping rim circumscribing the base-engaging surface, the stem-engaging proximal portion structured to receive the stem of the mandrel seated in the base-engaging distal portion via the aperture, and the member providing a barrier for preventing a silicone dispersion and/or texturing particles from contacting a base portion of the seated mandrel when the mandrel is immersed in the silicone dispersion and/or texturing particles for adhering the dispersion and/or particles to an exposed portion of the particle-coated, seated mandrel.

8. The assembly of claim 7 wherein the stem-engaging proximal portion defines a proximal portion cross-sectional profile and the base-engaging distal portion defines a distal portion cross-sectional profile, and the proximal portion cross-sectional profile is smaller than the distal portion cross-sectional profile.

9. A method for making a textured breast implant, the method comprising the steps of:

securing the member of claim 1 to the breast implant mandrel of claim 1 as covered with a silicone elastomer shell as the silicon elastomer;

coating the breast implant mandrel with a tacky elastomer;

immersing the breast implant mandrel and member secured thereto into a bath of texturing particles;

removing the member from the mandrel;

curing the tacky elastomer; and removing the texturing particles after the curing, the member providing a barrier for preventing the tacky elastomer and texturing particles from contacting the silicone elastomer shell over the base portion of the covered mandrel matingly sealed against the member during said coating and immersing steps.

10. The method of claim 9 further comprising, prior to the removing step, repeating the steps of coating and immersing to reach a desired texture thickness.

11. The method of claim 9 wherein the base-engaging surface of the member is a substantially conically shaped surface.

12. The method of claim 9 wherein the base-engaging surface is a substantially conically shaped surface and the aperture is disposed generally in the center of the conically shaped surface.

13. The method of claim 9 wherein the proximally sloping rim slopes at an angle substantially equal to a slope of an exposed portion of the matingly sealed mandrel which receives said coating and texturing particles such that the proximally sloping rim substantially aligns with the exposed portion when the mandrel is seated in the base-engaging portion by said securing.

14. A method for making a textured breast implant, the method comprising the steps of:

providing the breast implant mandrel of claim 7 with a particle-coated tacky surface;

securing the member of claim 7 to the breast implant mandrel such that the member covers a portion of the particle coating tacky surface;

immersing the breast implant mandrel and member secured thereto into an elastomeric dispersion to form an elastomer coating on the mandrel;

immersing the breast implant mandrel and member secured thereto into a bath of texturing particles;

removing the member from the mandrel;

curing the elastomer coating; and removing the texturing particles thereby producing a textured breast implant having a variable textured surface, the member providing a barrier for preventing the elastomeric dispersion and texturing particles from contacting the particle-coated tacky surface over a base portion of the particle-coated mandrel matingly sealed against the member during said immersing steps.

15. The method of claim 14 further comprising, after the step of immersing into the bath of texturing particles, repeating, at least once, the steps of immersing into the dispersion and immersing into the bath so as to form a layered elastomer and particle coating having a desired thickness.

* * * * *

UNITED STATES PATENT AND TRADEMARK OFFICE
CERTIFICATE OF CORRECTION

| | | |
|---|---|---|
| PATENT NO. | : 10,864,661 B2 | Page 1 of 1 |
| APPLICATION NO. | : 15/629635 | |
| DATED | : December 15, 2020 | |
| INVENTOR(S) | : Robert L. Nieto et al. | |

It is certified that error appears in the above-identified patent and that said Letters Patent is hereby corrected as shown below:

In the Claims

Please replace the term --silicon-- in Column 8, Line 9 Claim 9: with the term "silicone".

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*